(12) United States Patent
Spencer et al.

(10) Patent No.: US 8,267,892 B2
(45) Date of Patent: Sep. 18, 2012

(54) MULTI-LANGUAGE / MULTI-PROCESSOR INFUSION PUMP ASSEMBLY

(75) Inventors: Geoffrey P. Spencer, Manchester, NH (US); Robert J. Bryant, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 239 days.

(21) Appl. No.: 12/249,600

(22) Filed: Oct. 10, 2008

(65) Prior Publication Data

US 2010/0094221 A1 Apr. 15, 2010

(51) Int. Cl.
*A61M 1/00* (2006.01)
(52) U.S. Cl. .......................... 604/151; 604/131
(58) Field of Classification Search ............... 417/477.2; 600/431–435; 604/65–67, 118–121, 131–147, 604/151–155, 890.1–892.1
See application file for complete search history.

(56) References Cited

U.S. PATENT DOCUMENTS

| | | |
|---|---|---|
| 3,631,847 A | 1/1972 | Hobbs, II |
| 3,692,027 A | 9/1972 | Ellinwood, Jr. |
| 3,752,510 A | 8/1973 | Windischman et al. |
| 3,811,121 A | 5/1974 | Heim et al. |
| 3,811,122 A | 5/1974 | Raber et al. |
| 3,837,339 A | 9/1974 | Aisenberg et al. |
| 3,887,393 A | 6/1975 | La Rue, Jr. |
| 3,951,147 A | 4/1976 | Tucker et al. |
| D248,873 S | 8/1978 | Raitto |
| 4,123,631 A | 10/1978 | Lewis |
| 4,146,029 A | 3/1979 | Ellinwood, Jr. |
| 4,150,672 A | 4/1979 | Whitney et al. |
| D254,446 S | 3/1980 | Raitto |
| 4,206,274 A | 6/1980 | Peels |
| 4,215,701 A | 8/1980 | Raitto |
| 4,267,836 A | 5/1981 | Whitney et al. |
| 4,269,908 A | 5/1981 | Stemme |
| 4,270,532 A | 6/1981 | Franetzki et al. |
| 4,273,121 A | 6/1981 | Jassawalla |
| 4,282,872 A | 8/1981 | Franetzki et al. |
| 4,296,949 A | 10/1981 | Muetterties et al. |

(Continued)

FOREIGN PATENT DOCUMENTS

DE 4329229 A1 3/1995

(Continued)

OTHER PUBLICATIONS

International Search Report with Written Opinion, dated Mar. 23, 2010, received in international patent application No. PCT/US09/060158, 21 pgs.

(Continued)

*Primary Examiner* — Christopher D Koharski
*Assistant Examiner* — Gerald Landry, II
(74) *Attorney, Agent, or Firm* — McCormick, Paulding & Huber LLP

(57) ABSTRACT

An infusion pump assembly includes a reservoir assembly configured to contain an infusible fluid. A motor assembly is configured to act upon the reservoir assembly and dispense at least a portion of the infusible fluid contained within the reservoir assembly. Processing logic is configured to control the motor assembly. The processing logic includes a primary microprocessor configured to execute one or more primary applications written in a first computer language; and a safety microprocessor configured to execute one or more safety applications written in a second computer language.

21 Claims, 3 Drawing Sheets

U.S. PATENT DOCUMENTS

| | | | |
|---|---|---|---|
| 4,331,262 A | 5/1982 | Snyder et al. |
| 4,371,594 A | 2/1983 | Ohara et al. |
| 4,373,527 A | 2/1983 | Fischell |
| 4,391,883 A | 7/1983 | Williamson et al. |
| 4,392,847 A | 7/1983 | Whitney et al. |
| 4,392,849 A | 7/1983 | Petre et al. |
| 4,395,259 A | 7/1983 | Prestele et al. |
| 4,437,859 A | 3/1984 | Whitehouse et al. |
| 4,443,218 A | 4/1984 | DeCant, Jr. et al. |
| 4,464,170 A | 8/1984 | Clemens et al. |
| 4,469,481 A | 9/1984 | Kobayashi |
| 4,475,901 A | 10/1984 | Kraegen et al. |
| 4,493,704 A | 1/1985 | Beard et al. |
| 4,494,950 A | 1/1985 | Fischell |
| 4,498,843 A | 2/1985 | Schneider et al. |
| 4,533,346 A | 8/1985 | Cosgrove, Jr. et al. |
| 4,542,532 A | 9/1985 | McQuilkin |
| 4,543,093 A | 9/1985 | Christinger |
| 4,550,731 A | 11/1985 | Batina et al. |
| 4,559,037 A | 12/1985 | Franetzki et al. |
| 4,559,038 A | 12/1985 | Berg et al. |
| 4,562,751 A | 1/1986 | Nason et al. |
| 4,596,575 A | 6/1986 | Rosenberg et al. |
| 4,624,661 A | 11/1986 | Arimond |
| 4,633,878 A | 1/1987 | Bombardieri |
| 4,648,872 A | 3/1987 | Kamen |
| 4,673,396 A | 6/1987 | Urbaniak |
| 4,678,408 A | 7/1987 | Nason et al. |
| 4,685,903 A | 8/1987 | Cable et al. |
| 4,690,878 A | 9/1987 | Nakamura |
| 4,696,671 A | 9/1987 | Epstein et al. |
| 4,731,051 A | 3/1988 | Fischell |
| 4,731,726 A | 3/1988 | Allen, III |
| 4,735,441 A | 4/1988 | Stephens |
| 4,741,731 A | 5/1988 | Starck et al. |
| 4,743,895 A | 5/1988 | Alexander |
| 4,747,828 A | 5/1988 | Tseo |
| 4,790,028 A | 12/1988 | Ramage |
| 4,803,625 A | 2/1989 | Fu et al. |
| 4,804,368 A | 2/1989 | Skakoon et al. |
| 4,809,697 A | 3/1989 | Causey, III et al. |
| 4,826,810 A | 5/1989 | Aoki |
| 4,834,712 A | 5/1989 | Quinn et al. |
| 4,849,852 A | 7/1989 | Mullins |
| 4,856,340 A | 8/1989 | Garrison |
| 4,871,351 A | 10/1989 | Feingold |
| 4,880,712 A | 11/1989 | Gordecki |
| 4,881,063 A | 11/1989 | Fawcett |
| 4,898,578 A | 2/1990 | Rubalcaba, Jr. |
| 4,919,650 A | 4/1990 | Feingold et al. |
| 4,959,640 A | 9/1990 | Hall |
| 4,972,508 A | 11/1990 | King |
| 4,988,337 A | 1/1991 | Ito |
| 4,997,423 A | 3/1991 | Okuda et al. |
| 5,009,646 A | 4/1991 | Sudo et al. |
| 5,019,974 A | 5/1991 | Beckers |
| 5,034,004 A | 7/1991 | Crankshaw |
| 5,049,141 A | 9/1991 | Olive |
| 5,050,612 A | 9/1991 | Matsumura |
| 5,055,830 A | 10/1991 | Cousins et al. |
| 5,063,291 A | 11/1991 | Buehring |
| 5,078,683 A | 1/1992 | Sancoff et al. |
| 5,080,653 A | 1/1992 | Voss et al. |
| 5,088,981 A * | 2/1992 | Howson et al. ................. 604/31 |
| 5,101,814 A | 4/1992 | Palti |
| 5,102,388 A | 4/1992 | Richmond |
| 5,103,216 A | 4/1992 | Sisselman |
| 5,104,374 A | 4/1992 | Bishko et al. |
| 5,150,314 A | 9/1992 | Garratt et al. |
| 5,153,827 A | 10/1992 | Coutré et al. |
| 5,165,407 A | 11/1992 | Wilson et al. |
| 5,174,716 A | 12/1992 | Hora et al. |
| 5,176,502 A | 1/1993 | Sanderson et al. |
| 5,176,644 A | 1/1993 | Srisathapat et al. |
| 5,176,662 A | 1/1993 | Bartholomew et al. |
| 5,181,910 A | 1/1993 | Scanlon |
| 5,187,746 A | 2/1993 | Narisawa |
| 5,191,855 A | 3/1993 | Conforti |
| 5,197,322 A | 3/1993 | Indravudh |
| 5,197,895 A | 3/1993 | Stupecky |
| 5,205,819 A | 4/1993 | Ross et al. |
| 5,216,597 A | 6/1993 | Beckers |
| 5,217,442 A | 6/1993 | Davis |
| 5,248,569 A | 9/1993 | Pine et al. |
| 5,254,093 A | 10/1993 | Bartlett et al. |
| 5,254,096 A | 10/1993 | Rondelet et al. |
| 5,257,971 A | 11/1993 | Lord et al. |
| 5,257,980 A | 11/1993 | Van Antwerp et al. |
| 5,270,702 A | 12/1993 | Krolak |
| 5,290,639 A | 3/1994 | Mallory |
| 5,304,152 A | 4/1994 | Sams |
| 5,307,263 A | 4/1994 | Brown |
| 5,314,416 A | 5/1994 | Lewis et al. |
| 5,317,506 A | 5/1994 | Coutré et al. |
| 5,337,215 A | 8/1994 | Sunderland et al. |
| 5,338,157 A | 8/1994 | Blomquist |
| 5,339,821 A | 8/1994 | Fujimoto |
| 5,341,291 A | 8/1994 | Roizen et al. |
| 5,342,324 A | 8/1994 | Tucker |
| 5,349,852 A | 9/1994 | Kamen et al. |
| 5,350,411 A | 9/1994 | Ryan et al. |
| 5,357,427 A | 10/1994 | Langen et al. |
| 5,364,242 A | 11/1994 | Olsen |
| 5,364,346 A | 11/1994 | Schrezenmeir |
| 5,368,562 A | 11/1994 | Blomquist et al. |
| 5,370,622 A | 12/1994 | Livingston et al. |
| 5,372,133 A | 12/1994 | Hogen Esch |
| 5,376,070 A | 12/1994 | Purvis et al. |
| 5,383,865 A | 1/1995 | Michel |
| 5,389,078 A | 2/1995 | Zalesky et al. |
| 5,390,671 A | 2/1995 | Lord et al. |
| 5,391,157 A | 2/1995 | Harris et al. |
| 5,399,823 A | 3/1995 | McCusker |
| 5,403,648 A | 4/1995 | Chan et al. |
| 5,417,667 A | 5/1995 | Tennican et al. |
| 5,429,602 A | 7/1995 | Hauser |
| 5,433,710 A | 7/1995 | VanAntwerp et al. |
| 5,456,940 A | 10/1995 | Funderburk |
| 5,460,618 A | 10/1995 | Harreld |
| 5,462,525 A | 10/1995 | Srisathapat et al. |
| 5,464,392 A | 11/1995 | Epstein et al. |
| 5,466,218 A | 11/1995 | Srisathapat et al. |
| 5,472,317 A | 12/1995 | Field et al. |
| 5,476,460 A | 12/1995 | Montalvo |
| 5,478,211 A | 12/1995 | Dominiak et al. |
| 5,482,446 A | 1/1996 | Williamson et al. |
| 5,497,772 A | 3/1996 | Schulman et al. |
| 5,505,709 A | 4/1996 | Funderburk et al. |
| 5,507,727 A | 4/1996 | Crainich |
| 5,508,690 A | 4/1996 | Shur et al. |
| 5,514,097 A | 5/1996 | Knauer |
| 5,514,103 A | 5/1996 | Srisathapat et al. |
| 5,522,803 A | 6/1996 | Teissen-Simony |
| 5,526,844 A | 6/1996 | Kamen et al. |
| 5,527,307 A | 6/1996 | Srisathapat et al. |
| 5,528,359 A | 6/1996 | Taguchi |
| 5,531,697 A | 7/1996 | Olsen et al. |
| 5,531,698 A | 7/1996 | Olsen |
| 5,533,389 A | 7/1996 | Kamen et al. |
| 5,533,996 A | 7/1996 | Murphey et al. |
| 5,538,399 A | 7/1996 | Johnson |
| 5,540,564 A | 7/1996 | Klopfer |
| 5,543,588 A | 8/1996 | Bisset et al. |
| 5,545,140 A | 8/1996 | Conero et al. |
| 5,545,142 A | 8/1996 | Stephens et al. |
| 5,545,143 A | 8/1996 | Fischell |
| 5,545,152 A | 8/1996 | Funderburk et al. |
| 5,558,640 A | 9/1996 | Pfeiler et al. |
| 5,558,641 A | 9/1996 | Glantz et al. |
| 5,562,618 A | 10/1996 | Cai et al. |
| 5,564,915 A | 10/1996 | Johnson |
| 5,567,119 A | 10/1996 | Johnson |
| 5,567,136 A | 10/1996 | Johnson |
| 5,569,026 A | 10/1996 | Novak |
| 5,569,186 A | 10/1996 | Lord et al. |
| 5,569,187 A | 10/1996 | Kaiser |
| 5,573,506 A | 11/1996 | Vasko |

| Patent No. | Date | Inventor |
|---|---|---|
| 5,575,310 A | 11/1996 | Kamen et al. |
| 5,582,593 A | 12/1996 | Hultman |
| 5,584,813 A | 12/1996 | Livingston et al. |
| 5,593,390 A | 1/1997 | Castellano et al. |
| 5,594,638 A | 1/1997 | Iliff |
| 5,609,060 A | 3/1997 | Dent |
| 5,609,575 A | 3/1997 | Larson et al. |
| 5,613,945 A | 3/1997 | Cai et al. |
| 5,620,312 A | 4/1997 | Hyman et al. |
| 5,626,144 A | 5/1997 | Tacklind et al. |
| 5,630,710 A | 5/1997 | Tune et al. |
| 5,632,729 A | 5/1997 | Cai et al. |
| 5,637,095 A | 6/1997 | Nason et al. |
| 5,637,420 A | 6/1997 | Jones, Jr. et al. |
| 5,641,892 A | 6/1997 | Larkins et al. |
| 5,643,212 A | 7/1997 | Coutré et al. |
| 5,647,853 A | 7/1997 | Feldmann et al. |
| 5,647,854 A | 7/1997 | Olsen et al. |
| 5,651,775 A | 7/1997 | Walker et al. |
| 5,658,133 A | 8/1997 | Anderson et al. |
| 5,658,250 A | 8/1997 | Blomquist et al. |
| 5,658,252 A | 8/1997 | Johnson |
| 5,660,176 A | 8/1997 | Iliff |
| 5,665,065 A | 9/1997 | Colman et al. |
| 5,669,877 A | 9/1997 | Blomquist |
| 5,669,887 A | 9/1997 | Cooper |
| 5,678,568 A | 10/1997 | Uchikubo et al. |
| 5,681,285 A | 10/1997 | Ford et al. |
| 5,685,844 A * | 11/1997 | Marttila ............................ 604/65 |
| 5,687,734 A | 11/1997 | Dempsey et al. |
| 5,695,473 A | 12/1997 | Olsen |
| 5,704,366 A | 1/1998 | Tacklind et al. |
| 5,713,856 A | 2/1998 | Eggers et al. |
| 5,713,857 A | 2/1998 | Grimard et al. |
| 5,716,725 A | 2/1998 | Riveron et al. |
| 5,718,562 A | 2/1998 | Lawless et al. |
| 5,720,729 A | 2/1998 | Kriesel |
| 5,727,241 A | 3/1998 | Yamano et al. |
| 5,733,673 A | 3/1998 | Kunert |
| 5,743,873 A | 4/1998 | Cai et al. |
| 5,752,940 A | 5/1998 | Grimard |
| 5,755,744 A | 5/1998 | Shaw et al. |
| 5,762,632 A | 6/1998 | Whisson |
| 5,764,159 A | 6/1998 | Neftel |
| 5,772,409 A | 6/1998 | Johnson |
| 5,772,635 A | 6/1998 | Dastur et al. |
| 5,776,116 A | 7/1998 | Lopez et al. |
| 5,779,665 A | 7/1998 | Mastrototaro et al. |
| 5,785,681 A | 7/1998 | Indravudh |
| 5,788,669 A | 8/1998 | Peterson |
| 5,788,671 A | 8/1998 | Johnson |
| 5,788,673 A | 8/1998 | Young et al. |
| 5,788,678 A | 8/1998 | Van Antwerp |
| 5,795,337 A | 8/1998 | Grimard |
| 5,800,387 A | 9/1998 | Duffy et al. |
| 5,800,420 A | 9/1998 | Gross et al. |
| 5,801,600 A | 9/1998 | Butland et al. |
| 5,807,336 A | 9/1998 | Russo et al. |
| 5,810,001 A | 9/1998 | Genga et al. |
| 5,810,771 A | 9/1998 | Blomquist |
| 5,814,015 A | 9/1998 | Gargano et al. |
| 5,822,715 A | 10/1998 | Worthington et al. |
| 5,823,746 A | 10/1998 | Johnson |
| 5,832,448 A | 11/1998 | Brown |
| 5,840,020 A | 11/1998 | Heinonen et al. |
| 5,840,026 A | 11/1998 | Uber, III et al. |
| 5,843,146 A | 12/1998 | Cross, Jr. |
| 5,851,197 A | 12/1998 | Marano et al. |
| 5,851,692 A | 12/1998 | Potts |
| 5,861,018 A | 1/1999 | Feierbach |
| 5,868,669 A | 2/1999 | Iliff |
| 5,871,465 A | 2/1999 | Vasko |
| 5,876,370 A | 3/1999 | Blomquist |
| 5,879,143 A | 3/1999 | Cote et al. |
| 5,879,144 A | 3/1999 | Johnson |
| 5,879,163 A | 3/1999 | Brown et al. |
| 5,882,256 A | 3/1999 | Shropshire |
| 5,885,245 A | 3/1999 | Lynch et al. |
| 5,897,493 A | 4/1999 | Brown |
| 5,899,855 A | 5/1999 | Brown |
| 5,913,310 A | 6/1999 | Brown |
| 5,918,603 A | 7/1999 | Brown |
| 5,925,021 A | 7/1999 | Castellano et al. |
| 5,928,196 A | 7/1999 | Johnson et al. |
| 5,928,202 A | 7/1999 | Linnebjerg |
| 5,931,791 A | 8/1999 | Saltzstein et al. |
| 5,933,136 A | 8/1999 | Brown |
| 5,935,099 A | 8/1999 | Peterson et al. |
| 5,935,105 A | 8/1999 | Manning et al. |
| 5,935,106 A | 8/1999 | Olsen |
| 5,940,801 A | 8/1999 | Brown |
| 5,951,521 A | 9/1999 | Mastrototaro et al. |
| 5,954,485 A | 9/1999 | Johnson et al. |
| 5,954,697 A | 9/1999 | Srisathapat et al. |
| 5,954,700 A | 9/1999 | Kovelman |
| 5,956,501 A | 9/1999 | Brown |
| 5,957,890 A | 9/1999 | Mann et al. |
| 5,960,403 A | 9/1999 | Brown |
| 5,968,011 A | 10/1999 | Larsen et al. |
| 5,971,963 A | 10/1999 | Choi |
| 5,973,623 A | 10/1999 | Gupta et al. |
| 5,980,506 A | 11/1999 | Mathiasen |
| 5,989,216 A | 11/1999 | Johnson et al. |
| 5,989,227 A | 11/1999 | Vetter et al. |
| 5,997,476 A | 12/1999 | Brown |
| 6,007,941 A | 12/1999 | Hermann et al. |
| 6,009,339 A | 12/1999 | Bentsen et al. |
| 6,014,587 A | 1/2000 | Shaw et al. |
| 6,017,326 A | 1/2000 | Pasqualucci et al. |
| 6,017,328 A | 1/2000 | Fischell et al. |
| 6,024,539 A | 2/2000 | Blomquist |
| 6,032,119 A | 2/2000 | Brown et al. |
| 6,042,565 A | 3/2000 | Hirschman et al. |
| 6,056,522 A | 5/2000 | Johnson |
| 6,056,718 A | 5/2000 | Funderburk et al. |
| 6,059,753 A | 5/2000 | Faust et al. |
| 6,063,059 A | 5/2000 | Kriesel |
| 6,073,036 A | 6/2000 | Heikkinen et al. |
| 6,077,055 A | 6/2000 | Vilks |
| 6,086,575 A | 7/2000 | Mejslov |
| 6,090,081 A | 7/2000 | Sudo et al. |
| 6,093,172 A | 7/2000 | Funderburk et al. |
| 6,096,011 A | 8/2000 | Trombley, III et al. |
| 6,099,507 A | 8/2000 | Heinzerling |
| 6,101,478 A | 8/2000 | Brown |
| 6,110,152 A | 8/2000 | Kovelman |
| 6,112,111 A | 8/2000 | Glantz |
| 6,123,686 A | 9/2000 | Olsen et al. |
| 6,123,690 A | 9/2000 | Mejslov |
| 6,135,949 A | 10/2000 | Russo et al. |
| 6,165,154 A | 12/2000 | Gray et al. |
| 6,171,287 B1 | 1/2001 | Lynn et al. |
| 6,202,708 B1 | 3/2001 | Bynum |
| 6,206,856 B1 | 3/2001 | Mahurkar |
| 6,211,856 B1 | 4/2001 | Choi et al. |
| 6,216,795 B1 | 4/2001 | Buchl |
| 6,225,711 B1 | 5/2001 | Gupta et al. |
| 6,241,704 B1 | 6/2001 | Peterson et al. |
| 6,246,992 B1 | 6/2001 | Brown |
| 6,248,093 B1 | 6/2001 | Moberg |
| 6,253,804 B1 | 7/2001 | Safabash |
| 6,254,586 B1 | 7/2001 | Mann et al. |
| 6,259,587 B1 | 7/2001 | Sheldon et al. |
| 6,267,564 B1 | 7/2001 | Rapheal |
| 6,269,340 B1 | 7/2001 | Ford et al. |
| 6,270,455 B1 | 8/2001 | Brown |
| 6,280,416 B1 | 8/2001 | Van Antwerp et al. |
| 6,283,943 B1 | 9/2001 | Dy et al. |
| 6,293,159 B1 | 9/2001 | Kriesel et al. |
| 6,293,925 B1 | 9/2001 | Safabash et al. |
| 6,305,908 B1 | 10/2001 | Hermann et al. |
| 6,309,375 B1 | 10/2001 | Glines et al. |
| 6,311,868 B1 | 11/2001 | Krietemeier et al. |
| 6,321,158 B1 | 11/2001 | DeLorme et al. |
| 6,362,591 B1 | 3/2002 | Moberg |
| 6,364,859 B1 | 4/2002 | St. Romain et al. |
| 6,364,865 B1 | 4/2002 | Lavi et al. |
| 6,374,876 B2 | 4/2002 | Bynum |

| | | | | | | |
|---|---|---|---|---|---|---|
| 6,375,638 | B2 | 4/2002 | Nason et al. | 6,770,067 | B2 | 8/2004 | Lorenzen et al. |
| 6,416,293 | B1 | 7/2002 | Bouchard et al. | 6,772,650 | B2 | 8/2004 | Ohyama et al. |
| 6,422,057 | B1 | 7/2002 | Anderson | 6,800,071 | B1 | 10/2004 | McConnell et al. |
| 6,423,035 | B1 | 7/2002 | Das et al. | 6,801,420 | B2 | 10/2004 | Talbot et al. |
| 6,427,088 | B1 | 7/2002 | Bowman, IV et al. | 6,805,693 | B2 | 10/2004 | Gray et al. |
| 6,428,509 | B1 | 8/2002 | Fielder | 6,810,290 | B2 | 10/2004 | Lebel et al. |
| 6,447,481 | B1 | 9/2002 | Duchon et al. | 6,811,533 | B2 | 11/2004 | Lebel et al. |
| 6,453,956 | B2 | 9/2002 | Safabash | 6,811,534 | B2 | 11/2004 | Bowman, IV et al. |
| 6,458,102 | B1 | 10/2002 | Mann et al. | 6,813,519 | B2 | 11/2004 | Lebel et al. |
| 6,459,424 | B1 | 10/2002 | Resman | 6,817,990 | B2 | 11/2004 | Yap et al. |
| 6,461,329 | B1 | 10/2002 | Van Antwerp et al. | 6,827,702 | B2 | 12/2004 | Lebel et al. |
| 6,461,331 | B1 | 10/2002 | Van Antwerp | 6,830,558 | B2 | 12/2004 | Flaherty et al. |
| 6,466,203 | B2 | 10/2002 | Van Ee | 6,835,190 | B2 | 12/2004 | Nguyen |
| 6,475,180 | B2 | 11/2002 | Peterson et al. | 6,845,465 | B2 | 1/2005 | Hashemi |
| 6,475,196 | B1 | 11/2002 | Vachon | 6,852,104 | B2 | 2/2005 | Blomquist |
| 6,485,461 | B1 | 11/2002 | Mason et al. | 6,854,620 | B2 | 2/2005 | Ramey |
| 6,485,465 | B2 | 11/2002 | Moberg et al. | 6,872,200 | B2 | 3/2005 | Mann et al. |
| 6,520,938 | B1 | 2/2003 | Funderburk et al. | 6,873,268 | B2 | 3/2005 | Lebel et al. |
| 6,537,268 | B1 | 3/2003 | Gibson et al. | 6,879,930 | B2 | 4/2005 | Sinclair et al. |
| 6,549,423 | B1 | 4/2003 | Brodnick | 6,902,207 | B2 | 6/2005 | Lickliter |
| 6,551,276 | B1 | 4/2003 | Mann et al. | 6,916,010 | B2 | 7/2005 | Beck et al. |
| 6,551,277 | B1 | 4/2003 | Ford | 6,930,602 | B2 | 8/2005 | Villaseca et al. |
| 6,554,798 | B1 | 4/2003 | Mann et al. | 6,932,584 | B2 | 8/2005 | Gray et al. |
| 6,554,800 | B1 | 4/2003 | Nezhadian et al. | 6,936,029 | B2 | 8/2005 | Mann et al. |
| 6,555,986 | B2 | 4/2003 | Moberg | 6,945,760 | B2 | 9/2005 | Gray et al. |
| 6,558,320 | B1 | 5/2003 | Causey, III et al. | 6,950,708 | B2 | 9/2005 | Bowman, IV et al. |
| 6,558,351 | B1 | 5/2003 | Steil et al. | 6,951,551 | B2 | 10/2005 | Hudon |
| 6,562,001 | B2 | 5/2003 | Lebel et al. | 6,958,705 | B2 | 10/2005 | Lebel et al. |
| 6,562,023 | B1 | 5/2003 | Marrs et al. | 6,960,192 | B1 | 11/2005 | Flaherty et al. |
| 6,564,105 | B2 | 5/2003 | Starkweather et al. | 6,960,195 | B2 | 11/2005 | Heinz et al. |
| 6,571,128 | B2 | 5/2003 | Lebel et al. | 6,964,643 | B2 | 11/2005 | Hovland et al. |
| 6,572,542 | B1 | 6/2003 | Houben et al. | 6,974,437 | B2 | 12/2005 | Lebel et al. |
| 6,572,586 | B1 | 6/2003 | Wojcik | 6,978,517 | B2 | 12/2005 | Collins et al. |
| 6,577,899 | B2 | 6/2003 | Lebel et al. | 6,979,326 | B2 | 12/2005 | Mann et al. |
| RE38,189 | E | 7/2003 | Walker et al. | 6,994,619 | B2 | 2/2006 | Scholten |
| 6,585,644 | B2 | 7/2003 | Lebel et al. | 6,997,905 | B2 | 2/2006 | Gillespie, Jr. et al. |
| 6,585,695 | B1 | 7/2003 | Adair et al. | 6,997,907 | B2 | 2/2006 | Safabash et al. |
| 6,591,876 | B2 | 7/2003 | Safabash | 6,997,910 | B2 | 2/2006 | Howlett et al. |
| 6,592,551 | B1 | 7/2003 | Cobb | 6,997,920 | B2 | 2/2006 | Mann et al. |
| 6,595,756 | B2 | 7/2003 | Gray et al. | 6,997,921 | B2 | 2/2006 | Gray et al. |
| 6,607,509 | B2 | 8/2003 | Bobroff et al. | 6,999,854 | B2 | 2/2006 | Roth |
| 6,613,015 | B2 | 9/2003 | Sandstrom et al. | 7,011,608 | B2 | 3/2006 | Spencer |
| D480,477 | S | 10/2003 | Bush et al. | 7,018,360 | B2 | 3/2006 | Flaherty et al. |
| 6,641,533 | B2 | 11/2003 | Causey, III et al. | 7,021,560 | B2 | 4/2006 | Gray et al. |
| 6,642,936 | B1 | 11/2003 | Engholm et al. | 7,024,245 | B2 | 4/2006 | Lebel et al. |
| 6,645,177 | B1 | 11/2003 | Shearn | 7,025,226 | B2 | 4/2006 | Ramey |
| 6,648,821 | B2 | 11/2003 | Lebel et al. | 7,025,743 | B2 | 4/2006 | Mann et al. |
| 6,652,493 | B1 | 11/2003 | Das | 7,029,455 | B2 | 4/2006 | Flaherty |
| 6,652,510 | B2 | 11/2003 | Lord et al. | 7,029,456 | B2 | 4/2006 | Ware et al. |
| 6,656,148 | B2 | 12/2003 | Das et al. | 7,033,338 | B2 | 4/2006 | Vilks et al. |
| 6,656,158 | B2 | 12/2003 | Mahoney et al. | 7,033,339 | B1 | 4/2006 | Lynn |
| 6,656,159 | B2 | 12/2003 | Flaherty | 7,041,082 | B2 | 5/2006 | Blomquist et al. |
| 6,659,948 | B2 | 12/2003 | Lebel et al. | 7,045,361 | B2 | 5/2006 | Heiss et al. |
| 6,665,909 | B2 | 12/2003 | Collins et al. | 7,046,230 | B2 | 5/2006 | Zadesky et al. |
| 6,669,669 | B2 | 12/2003 | Flaherty et al. | 7,050,927 | B2 | 5/2006 | Sinclair et al. |
| 6,684,058 | B1 | 1/2004 | Karacaoglu et al. | 7,052,251 | B2 | 5/2006 | Nason et al. |
| 6,685,678 | B2 | 2/2004 | Evans et al. | 7,052,483 | B2 | 5/2006 | Wojcik |
| 6,687,546 | B2 | 2/2004 | Lebel et al. | 7,061,140 | B2 | 6/2006 | Zhang et al. |
| 6,689,091 | B2 | 2/2004 | Bui et al. | 7,063,684 | B2 | 6/2006 | Moberg |
| 6,691,043 | B2 | 2/2004 | Ribeiro, Jr. | 7,066,029 | B2 | 6/2006 | Beavis et al. |
| 6,692,457 | B2 | 2/2004 | Flaherty | 7,074,209 | B2 | 7/2006 | Evans et al. |
| 6,694,191 | B2 | 2/2004 | Starkweather et al. | 7,075,512 | B1 | 7/2006 | Fabre et al. |
| 6,699,218 | B2 | 3/2004 | Flaherty et al. | 7,098,803 | B2 | 8/2006 | Mann et al. |
| 6,704,034 | B1 | 3/2004 | Rodriguez et al. | 7,109,878 | B2 | 9/2006 | Mann et al. |
| 6,716,195 | B2 | 4/2004 | Nolan, Jr. et al. | 7,115,113 | B2 | 10/2006 | Evans et al. |
| 6,723,072 | B2 | 4/2004 | Flaherty et al. | 7,131,967 | B2 | 11/2006 | Gray et al. |
| 6,733,446 | B2 | 5/2004 | Lebel et al. | 7,137,964 | B2 | 11/2006 | Flaherty |
| 6,740,059 | B2 | 5/2004 | Flaherty | 7,144,384 | B2 | 12/2006 | Gorman et al. |
| 6,740,072 | B2 | 5/2004 | Starkweather et al. | 7,146,977 | B2 | 12/2006 | Beavis et al. |
| 6,740,075 | B2 | 5/2004 | Lebel et al. | 7,278,983 | B2 * | 10/2007 | Ireland et al. .................. 604/66 |
| 6,743,205 | B2 | 6/2004 | Nolan, Jr. et al. | 7,303,549 | B2 | 12/2007 | Flaherty et al. |
| 6,744,350 | B2 | 6/2004 | Blomquist | 7,305,984 | B2 | 12/2007 | Altobelli et al. |
| 6,749,586 | B2 | 6/2004 | Vasko | 7,306,578 | B2 | 12/2007 | Gray et al. |
| 6,749,587 | B2 | 6/2004 | Flaherty | 7,342,660 | B2 | 3/2008 | Altobelli et al. |
| 6,752,299 | B2 | 6/2004 | Shetler et al. | 7,498,563 | B2 | 3/2009 | Mandro et al. |
| 6,752,785 | B2 | 6/2004 | Van Antwerp et al. | 7,682,338 | B2 | 3/2010 | Griffin |
| 6,752,787 | B1 | 6/2004 | Causey, III et al. | 7,927,314 | B2 | 4/2011 | Kuracina et al. |
| 6,758,810 | B2 | 7/2004 | Lebel et al. | 8,016,789 | B2 | 9/2011 | Grant et al. |
| 6,768,425 | B2 | 7/2004 | Flaherty et al. | 2001/0034502 | A1 | 10/2001 | Moberg et al. |

| | | | | | | |
|---|---|---|---|---|---|---|
| 2001/0041869 A1 | 11/2001 | Causey, III et al. | | 2005/0055244 A1 | 3/2005 | Mullan et al. |
| 2001/0056258 A1 | 12/2001 | Evans | | 2005/0062732 A1 | 3/2005 | Sinclair et al. |
| 2002/0002326 A1 | 1/2002 | Causey, III et al. | | 2005/0063857 A1 | 3/2005 | Alheidt et al. |
| 2002/0013613 A1 | 1/2002 | Haller et al. | | 2005/0065464 A1 | 3/2005 | Talbot et al. |
| 2002/0022807 A1 | 2/2002 | Duchon et al. | | 2005/0065817 A1 | 3/2005 | Mihai et al. |
| 2002/0038392 A1 | 3/2002 | De La Huerga | | 2005/0069425 A1 | 3/2005 | Gray et al. |
| 2002/0043951 A1 | 4/2002 | Moberg | | 2005/0085760 A1 | 4/2005 | Ware et al. |
| 2002/0052539 A1 | 5/2002 | Haller et al. | | 2005/0096593 A1 | 5/2005 | Pope et al. |
| 2002/0052574 A1 | 5/2002 | Hochman et al. | | 2005/0137530 A1 | 6/2005 | Campbell et al. |
| 2002/0056114 A1 | 5/2002 | Fillebrown et al. | | 2005/0137573 A1 | 6/2005 | McLaughlin |
| 2002/0077852 A1 | 6/2002 | Ford et al. | | 2005/0148938 A1 | 7/2005 | Blomquist |
| 2002/0082665 A1 | 6/2002 | Haller et al. | | 2005/0171512 A1 | 8/2005 | Flaherty |
| 2002/0091454 A1 | 7/2002 | Vasko | | 2005/0171513 A1 | 8/2005 | Mann et al. |
| 2002/0107481 A1 | 8/2002 | Reilly et al. | | 2005/0177111 A1 | 8/2005 | Ozeri et al. |
| 2002/0123672 A1 | 9/2002 | Christophersom et al. | | 2005/0182366 A1 | 8/2005 | Vogt et al. |
| 2002/0126036 A1 | 9/2002 | Flaherty et al. | | 2005/0182389 A1 | 8/2005 | LaPorte et al. |
| 2002/0143290 A1 | 10/2002 | Bui et al. | | 2005/0187515 A1 | 8/2005 | Varrichio et al. |
| 2002/0158838 A1 | 10/2002 | Smith et al. | | 2005/0187593 A1 | 8/2005 | Housworth et al. |
| 2002/0169439 A1 | 11/2002 | Flaherty | | 2005/0192494 A1 | 9/2005 | Ginsberg |
| 2002/0173748 A1 | 11/2002 | McConnell et al. | | 2005/0203461 A1 | 9/2005 | Flaherty et al. |
| 2002/0193679 A1 | 12/2002 | Malave et al. | | 2005/0215982 A1 | 9/2005 | Malave et al. |
| 2002/0193846 A1 | 12/2002 | Pool et al. | | 2005/0224705 A1 | 10/2005 | Tobiason et al. |
| 2003/0009133 A1 | 1/2003 | Ramey | | 2005/0234404 A1 | 10/2005 | Vilks et al. |
| 2003/0014013 A1 | 1/2003 | Choi | | 2005/0238503 A1 | 10/2005 | Rush et al. |
| 2003/0028079 A1 | 2/2003 | Lebel et al. | | 2005/0238507 A1 | 10/2005 | DiIanni et al. |
| 2003/0028346 A1 | 2/2003 | Sinclair et al. | | 2005/0245904 A1 | 11/2005 | Estes et al. |
| 2003/0065308 A1 | 4/2003 | Lebel et al. | | 2005/0250368 A1 | 11/2005 | Singer et al. |
| 2003/0076306 A1 | 4/2003 | Zadesky et al. | | 2005/0261660 A1 | 11/2005 | Choi |
| 2003/0088238 A1 | 5/2003 | Poulsen et al. | | 2005/0263615 A1 | 12/2005 | Kriesel et al. |
| 2003/0114836 A1 | 6/2003 | Estes et al. | | 2005/0267363 A1 | 12/2005 | Duchon et al. |
| 2003/0125672 A1 | 7/2003 | Adair et al. | | 2005/0267550 A1 | 12/2005 | Hess et al. |
| 2003/0130618 A1 | 7/2003 | Gray et al. | | 2005/0267928 A1 * | 12/2005 | Anderson et al. ............ 709/200 |
| 2003/0132922 A1 | 7/2003 | Philipp | | 2005/0273059 A1 | 12/2005 | Mernoe et al. |
| 2003/0141981 A1 | 7/2003 | Bui et al. | | 2005/0285880 A1 | 12/2005 | Lai et al. |
| 2003/0161744 A1 | 8/2003 | Vilks et al. | | 2006/0016800 A1 | 1/2006 | Paradiso et al. |
| 2003/0163089 A1 | 8/2003 | Bynum | | 2006/0025663 A1 | 2/2006 | Talbot et al. |
| 2003/0163090 A1 | 8/2003 | Blomquist et al. | | 2006/0026535 A1 | 2/2006 | Hotelling et al. |
| 2003/0187525 A1 | 10/2003 | Mann et al. | | 2006/0026536 A1 | 2/2006 | Hotelling et al. |
| 2003/0191431 A1 | 10/2003 | Mann et al. | | 2006/0038791 A1 | 2/2006 | Mackey |
| 2003/0195462 A1 | 10/2003 | Mann et al. | | 2006/0041229 A1 | 2/2006 | Garibotto et al. |
| 2003/0212364 A1 | 11/2003 | Mann et al. | | 2006/0065772 A1 | 3/2006 | Grant et al. |
| 2003/0212379 A1 | 11/2003 | Bylund et al. | | 2006/0066581 A1 | 3/2006 | Lyon et al. |
| 2003/0229311 A1 | 12/2003 | Morris et al. | | 2006/0097991 A1 | 5/2006 | Hotelling et al. |
| 2003/0233069 A1 | 12/2003 | Gillespie, Jr. et al. | | 2006/0100591 A1 | 5/2006 | Alheidt et al. |
| 2004/0003493 A1 | 1/2004 | Adair et al. | | 2006/0106346 A1 | 5/2006 | Sullivan et al. |
| 2004/0054326 A1 | 3/2004 | Hommann et al. | | 2006/0123884 A1 | 6/2006 | Selker et al. |
| 2004/0059315 A1 | 3/2004 | Erickson et al. | | 2006/0129112 A1 | 6/2006 | Lynn |
| 2004/0064088 A1 | 4/2004 | Gorman et al. | | 2006/0144942 A1 | 7/2006 | Evans et al. |
| 2004/0068230 A1 | 4/2004 | Estes et al. | | 2006/0160670 A1 | 7/2006 | Spencer |
| 2004/0073095 A1 | 4/2004 | Causey, III et al. | | 2006/0161870 A1 | 7/2006 | Hotelling et al. |
| 2004/0073161 A1 | 4/2004 | Tachibana | | 2006/0161871 A1 | 7/2006 | Hotelling et al. |
| 2004/0082908 A1 | 4/2004 | Whitehurst et al. | | 2006/0173406 A1 | 8/2006 | Hayes et al. |
| 2004/0082918 A1 | 4/2004 | Evans et al. | | 2006/0173744 A1 * | 8/2006 | Choy et al. .................. 604/891.1 |
| 2004/0085215 A1 | 5/2004 | Moberg et al. | | 2006/0178633 A1 | 8/2006 | Garibotto et al. |
| 2004/0092873 A1 | 5/2004 | Moberg | | 2006/0178836 A1 | 8/2006 | Bai et al. |
| 2004/0116893 A1 | 6/2004 | Spohn et al. | | 2006/0184084 A1 * | 8/2006 | Ware et al. ................... 604/5.01 |
| 2004/0121767 A1 | 6/2004 | Simpson et al. | | 2006/0184123 A1 | 8/2006 | Gillespie, Jr. et al. |
| 2004/0127958 A1 | 7/2004 | Mazar et al. | | 2006/0184154 A1 | 8/2006 | Moberg et al. |
| 2004/0133166 A1 | 7/2004 | Moberg et al. | | 2006/0200257 A1 | 9/2006 | Kirste et al. |
| 2004/0135078 A1 | 7/2004 | Mandro et al. | | 2006/0227117 A1 | 10/2006 | Proctor |
| 2004/0140304 A1 | 7/2004 | Leyendecker | | 2006/0229557 A1 | 10/2006 | Fathallah et al. |
| 2004/0158193 A1 | 8/2004 | Bui et al. | | 2006/0232554 A1 | 10/2006 | Wong et al. |
| 2004/0162528 A1 | 8/2004 | Horvath et al. | | 2006/0236262 A1 | 10/2006 | Bathiche et al. |
| 2004/0167464 A1 | 8/2004 | Ireland et al. | | 2006/0236263 A1 | 10/2006 | Bathiche et al. |
| 2004/0172301 A1 | 9/2004 | Mihai et al. | | 2006/0253085 A1 | 11/2006 | Geismar et al. |
| 2004/0176667 A1 | 9/2004 | Mihai et al. | | 2006/0264894 A1 | 11/2006 | Moberg et al. |
| 2004/0176725 A1 | 9/2004 | Stutz et al. | | 2006/0282290 A1 | 12/2006 | Flaherty et al. |
| 2004/0193090 A1 | 9/2004 | Lebel et al. | | 2007/0049870 A1 | 3/2007 | Gray et al. |
| 2004/0207404 A1 | 10/2004 | Zhang et al. | | 2007/0060872 A1 | 3/2007 | Hall et al. |
| 2004/0235446 A1 | 11/2004 | Flaherty et al. | | 2007/0066956 A1 | 3/2007 | Finkel |
| 2004/0243065 A1 | 12/2004 | McConnell et al. | | 2007/0093750 A1 | 4/2007 | Jan et al. |
| 2005/0015056 A1 | 1/2005 | Duchon et al. | | 2007/0112298 A1 | 5/2007 | Mueller, Jr. et al. |
| 2005/0021000 A1 | 1/2005 | Adair et al. | | 2007/0118405 A1 | 5/2007 | Campbell et al. |
| 2005/0022274 A1 | 1/2005 | Campbell et al. | | 2007/0161955 A1 | 7/2007 | Bynum et al. |
| 2005/0027254 A1 | 2/2005 | Vasko | | 2007/0167905 A1 | 7/2007 | Estes et al. |
| 2005/0035956 A1 | 2/2005 | Sinclair et al. | | 2007/0178776 A1 | 8/2007 | Etter et al. |
| 2005/0048900 A1 | 3/2005 | Scholten | | 2007/0191770 A1 | 8/2007 | Moberg et al. |
| 2005/0052429 A1 | 3/2005 | Philipp | | 2007/0219480 A1 | 9/2007 | Kamen et al. |
| 2005/0055242 A1 | 3/2005 | Bello et al. | | 2007/0219496 A1 * | 9/2007 | Kamen et al. ................ 604/131 |

| | | | |
|---|---|---|---|
| 2007/0219597 A1 | 9/2007 | Kamen et al. | |
| 2007/0228071 A1 | 10/2007 | Kamen et al. | |
| 2007/0255250 A1 | 11/2007 | Moberg et al. | |
| 2007/0258395 A1 | 11/2007 | Jollota et al. | |
| 2008/0009824 A1 | 1/2008 | Moberg et al. | |
| 2008/0051710 A1 | 2/2008 | Moberg et al. | |
| 2008/0051711 A1 | 2/2008 | Mounce et al. | |
| 2008/0097321 A1 | 4/2008 | Mounce et al. | |
| 2008/0097328 A1 | 4/2008 | Moberg et al. | |
| 2008/0125701 A1 | 5/2008 | Moberg et al. | |
| 2008/0160492 A1 | 7/2008 | Campbell et al. | |
| 2008/0161754 A1* | 7/2008 | Marano-Ford | 604/67 |
| 2008/0177900 A1 | 7/2008 | Grant et al. | |
| 2009/0036870 A1 | 2/2009 | Mounce et al. | |
| 2009/0062767 A1 | 3/2009 | Van Antwerp et al. | |
| 2009/0062778 A2 | 3/2009 | Bengtsson et al. | |
| 2009/0069749 A1 | 3/2009 | Miller et al. | |
| 2009/0099523 A1 | 4/2009 | Grant et al. | |
| 2009/0164251 A1* | 6/2009 | Hayter | 705/3 |
| 2009/0171291 A1 | 7/2009 | Bente, IV et al. | |
| 2009/0234213 A1 | 9/2009 | Hayes et al. | |
| 2009/0259217 A1* | 10/2009 | Hyde et al. | 604/891.1 |
| 2009/0270811 A1 | 10/2009 | Mounce et al. | |
| 2010/0063445 A1 | 3/2010 | Sternberg et al. | |

FOREIGN PATENT DOCUMENTS

| | | |
|---|---|---|
| DE | 19627619 A1 | 1/1998 |
| DE | 20110059 A1 | 8/2002 |
| EP | 0256694 A1 | 2/1988 |
| EP | 0258566 A2 | 3/1988 |
| EP | 0338671 A1 | 10/1989 |
| EP | 0398394 A2 | 11/1990 |
| EP | 0554995 B1 | 8/1993 |
| EP | 0749757 A2 | 12/1996 |
| EP | 0763368 A2 | 3/1997 |
| EP | 0806738 A1 | 11/1997 |
| EP | 0830597 B1 | 3/1998 |
| EP | 0917882 A1 | 5/1999 |
| EP | 1109586 B1 | 6/2001 |
| EP | 1177802 A1 | 2/2002 |
| EP | 1338295 A1 | 8/2003 |
| EP | 1473050 A1 | 3/2004 |
| EP | 1115435 B1 | 8/2005 |
| EP | 1347705 B1 | 12/2005 |
| EP | 1 007 137 | 4/2006 |
| EP | 1688085 A1 | 8/2006 |
| EP | 1839694 A1 | 10/2007 |
| GB | 2218831 A | 11/1989 |
| WO | 94/08647 A1 | 4/1994 |
| WO | 95/24229 A2 | 9/1995 |
| WO | 95/28878 A1 | 11/1995 |
| WO | 95/31233 A1 | 11/1995 |
| WO | 96/08281 A1 | 3/1996 |
| WO | 96/14100 A1 | 5/1996 |
| WO | 96/20745 A1 | 7/1996 |
| WO | 96/36389 A1 | 11/1996 |
| WO | 97/21456 A1 | 6/1997 |
| WO | 97/40482 A1 | 10/1997 |
| WO | 9817336 A1 | 4/1998 |
| WO | 98/20439 A1 | 5/1998 |
| WO | 98/24358 A2 | 6/1998 |
| WO | WO 98/14234 | 9/1998 |
| WO | 98/42407 A1 | 10/1998 |
| WO | 98/49659 A2 | 11/1998 |
| WO | 98/58693 A1 | 12/1998 |
| WO | 98/59487 A1 | 12/1998 |
| WO | 99/08183 A1 | 2/1999 |
| WO | 99/10801 A1 | 3/1999 |
| WO | 99/18532 A1 | 4/1999 |
| WO | 99/22236 A1 | 5/1999 |
| WO | 99/44655 A2 | 9/1999 |
| WO | 99/59663 A1 | 11/1999 |
| WO | 00/10628 A2 | 3/2000 |
| WO | 00/28217 A1 | 5/2000 |
| WO | 00/69493 A1 | 11/2000 |
| WO | 01/00261 A1 | 1/2001 |
| WO | 01/61616 A3 | 8/2001 |
| WO | 01/70304 A1 | 9/2001 |
| WO | 02/04047 A2 | 1/2002 |
| WO | 02/24257 A1 | 3/2002 |
| WO | 02/49509 A2 | 6/2002 |
| WO | 02/053220 A2 | 7/2002 |
| WO | 02/056945 A2 | 7/2002 |
| WO | 02/070049 A1 | 9/2002 |
| WO | 02083209 A1 | 10/2002 |
| WO | 03/053498 A2 | 7/2003 |
| WO | 03/059422 A1 | 7/2003 |
| WO | 03/063932 A2 | 8/2003 |
| WO | 03/071930 A2 | 9/2003 |
| WO | 03/090838 A1 | 11/2003 |
| WO | 03/094075 A1 | 11/2003 |
| WO | 2004/007133 A1 | 1/2004 |
| WO | 2004/008956 A2 | 1/2004 |
| WO | 2004/009160 A1 | 1/2004 |
| WO | 2004006981 A2 | 1/2004 |
| WO | 2004-028596 A1 | 4/2004 |
| WO | 2004/058327 A2 | 7/2004 |
| WO | 2004/069095 A2 | 8/2004 |
| WO | 2004/070548 A2 | 8/2004 |
| WO | 2004/070557 A2 | 8/2004 |
| WO | 2004/070994 A2 | 8/2004 |
| WO | 2004/070995 A2 | 8/2004 |
| WO | 2004/098390 A2 | 11/2004 |
| WO | 2005/000378 A1 | 1/2005 |
| WO | 2005/010796 A2 | 2/2005 |
| WO | 2005/016411 A2 | 2/2005 |
| WO | 2005/019766 A2 | 3/2005 |
| WO | 2005/019987 A2 | 3/2005 |
| WO | WO 2005/039671 | 6/2005 |
| WO | 2005/094920 A1 | 10/2005 |
| WO | 2005/101279 A2 | 10/2005 |
| WO | 2005-102416 A1 | 11/2005 |
| WO | 2005/112899 A2 | 12/2005 |
| WO | 2005/121938 A2 | 12/2005 |
| WO | 2006/001929 A1 | 1/2006 |
| WO | 2006/023147 A2 | 3/2006 |
| WO | 2006/032652 A1 | 3/2006 |
| WO | 2006/081975 A1 | 8/2006 |
| WO | 2006/083831 A1 | 8/2006 |
| WO | 2006/097453 A1 | 9/2006 |
| WO | 2006/108809 A1 | 10/2006 |
| WO | 2007/016145 A1 | 2/2007 |

OTHER PUBLICATIONS

International Search Report and Written Opinion From Corresponding International Application No. PCT/US2007/003490, dated Nov. 28, 2007 (20 pages).

International Search Report and Written Opinion From Corresponding International Application No. PCT/US2007/003567, dated Oct. 17, 2007 (18 pages).

International Search Report and Written Opinion From Corresponding International Application No. PCT/US2007/003587, Nov. 12, 2007 (18 pages).

International Search Report and Written Opinion From Corresponding International Application No. PCT/US2007/003634, Oct. 2, 2007 (18 pages).

International Search Report From Corresponding International Application No. PCT/US2009/060158, dated Mar. 23, 2010 (7 pages).

International Search Report and Written Opinion From Corresponding International Application No. PCT/US2009/093169, dated Mar. 31, 2010 (23 pages).

International Preliminary Report on Patentability From Corresponding International Application No. PCT/US2007/003567, dated Aug. 21, 2008 (11 pages).

Extended European Search Report From European Application No. 09075460.7, dated Mar. 5, 2010 (14 pages).

Office Action from Japanese Appln. No. 2002-591067 dated Jun. 10, 2008 (4 pages).

Non-final Office Action from corresponding U.S. Appl. No. 12/249,891, dated Nov. 18, 2009 (15 pages).

Search Report from corresponding EP Appln. No. 10075446.4 dated Aug. 25, 2011 (10 pages).

Search Report from corresponding International Appln. No. PCT/US2011/030553 dated Dec. 23, 2011 (12 pages).
Conical fittings with a 6% (Luer) taper for syringes, needles and certain other medical equipment—Lock fittings, British Standard, BS EN 1707: 1997 (20 pages).
Conical fittings with a 6% (Luer) taper for syringes, needles and certain other medical equipment, Part 1. General requirements, British Standard, BS EN 20594-1 : 1994 ISO 594-1 : 1986 (17 pages).

* cited by examiner

MULTI-LANGUAGE / MULTI-PROCESSOR INFUSION PUMP ASSEMBLY

TECHNICAL FIELD

This disclosure relates to infusion pump assemblies and, more particularly, to infusion pump assemblies that include multiple microprocessors.

BACKGROUND

An infusion pump assembly may be used to infuse a fluid (e.g., a medication or nutrient) into a user. The fluid may be infused intravenously (i.e., into a vein), subcutaneously (i.e., into the skin), arterially (i.e., into an artery), and epidurally (i.e., into the epidural space).

Infusion pump assemblies may administer fluids in ways that would be impractically expensive/unreliable if performed manually by nursing staff. For example, an infusion pump assembly may repeatedly administer small quantities of an infusible fluid (e.g., 0.1 mL per hour), while allowing the user to request one-time larger "bolus" doses.

Unfortunately, the failure of a microprocessor included within a single-processor infusion pump assembly may result in the infusion pump assembly ceasing to operate. Additionally, in an infusion pump assembly that includes multiple microprocessors executing code written in a common language, an undisclosed problem within the common-language code may compromise the operation of all microprocessors included within the multi-processor infusion pump assembly.

SUMMARY OF DISCLOSURE

In a first implementation, an infusion pump assembly includes a reservoir assembly configured to contain an infusible fluid. A motor assembly is configured to act upon the reservoir assembly and dispense at least a portion of the infusible fluid contained within the reservoir assembly. Processing logic is configured to provide one or more control signals to the motor assembly. The one or more control signals are processable by the motor assembly to effectuate the dispensing of the at least a portion of the infusible fluid contained within the reservoir assembly. The processing logic includes a primary microprocessor configured to execute one or more primary applications written in a first computer language; and a safety microprocessor configured to execute one or more safety applications written in a second computer language.

One or more of the following features may be included. A primary power supply may be configured to provide primary electrical energy to at least a portion of the processing logic. A backup power supply may be configured to provide backup electrical energy to the at least a portion of the processing logic in the event that the primary power supply fails to provide the primary electrical energy to the at least a portion of the processing logic. The primary power supply may be a first battery; and the backup power supply may be a super capacitor assembly.

The processing logic may include one or more circuit partitioning components configured to divide the processing logic into primary processing logic and backup processing logic. The primary processing logic may include the primary microprocessor. The backup processing logic may include the safety microprocessor.

The one or more circuit partitioning components may include one or more of a diode assembly and a current limiting assembly. The diode assembly may be configured to allow the primary power supply to charge the backup power supply while prohibiting the backup power supply from providing backup electrical energy to the primary processing logic in the event that the primary power supply fails to provide the primary electrical energy to the primary processing logic.

The one or more primary applications written in the first computer language may be chosen from the group consisting of an operating system, an executive loop and a software application. The one or more safety applications written in the second computer language may be chosen from the group consisting of an operating system, an executive loop and a software application.

The primary power supply may be configured to provide electrical energy to one or more subsystems included within the infusion pump assembly. The primary power supply and the backup power supply may be configured to provide electrical energy to an audio system included within the infusion pump assembly. The audio system may be configured to provide an escalating alarm sequence in the event of a loss of a beacon signal, wherein the escalating alarm sequence includes at least a low-intensity alarm and a high-intensity alarm.

The first computer language may be chosen from the group consisting of Ada, Basic, Cobol, C, C++, C#, Fortran, Visual Assembler, Visual Basic, Visual J++, Java, and Java Script. The second computer language may be chosen from the group consisting of Ada, Basic, Cobol, C, C++, C#, Fortran, Visual Assembler, Visual Basic, Visual J++, Java, and Java Script.

In another implementation, an infusion pump assembly includes a reservoir assembly configured to contain an infusible fluid. A motor assembly is configured to act upon the reservoir assembly and dispense at least a portion of the infusible fluid contained within the reservoir assembly. Processing logic is configured to provide one or more control signals to the motor assembly. The one or more control signals are processable by the motor assembly to effectuate the dispensing of the at least a portion of the infusible fluid contained within the reservoir assembly. The processing logic includes one or more circuit partitioning components configured to divide the processing logic into primary processing logic and backup processing logic. A primary microprocessor is included within the primary processing logic and configured to execute one or more primary applications written in a first computer language. A safety microprocessor is included within the backup processing logic and configured to execute one or more safety applications written in a second computer language.

One or more of the following features may be included. The one or more primary applications written in the first computer language may be chosen from the group consisting of an operating system, an executive loop and a software application. The one or more safety applications written in the second computer language may be chosen from the group consisting of an operating system, an executive loop and a software application. A primary power supply may be configured to provide primary electrical energy to at least a portion of the processing logic. A backup power supply may be configured to provide backup electrical energy to the at least a portion of the processing logic in the event that the primary power supply fails to provide the primary electrical energy to the at least a portion of the processing logic.

The first computer language may be chosen from the group consisting of Ada, Basic, Cobol, C, C++, C#, Fortran, Visual Assembler, Visual Basic, Visual J++, Java, and Java Script. The second computer language may be chosen from the group consisting of Ada, Basic, Cobol, C, C++, C#, Fortran, Visual Assembler, Visual Basic, Visual J++, Java, and Java Script.

In another implementation, a computer program product resides on a computer readable medium having a plurality of instructions stored on it. When executed by a processor, the instructions cause the processor to perform operations including receiving, on a first microprocessor executing one or more applications written in a first computer language, an initial command processable by the one or more applications written in the first computer language. The initial command is converted into a modified command processable by one or more applications written in a second computer language. The modified command is provided to a second microprocessor executing the one or more applications written in the second computer language.

One or more of the following features may be included. The one or more applications written in the first computer language may be chosen from the group consisting of an operating system, an executive loop and a software application. The one or more applications written in the second computer language may be chosen from the group consisting of an operating system, an executive loop and a software application.

The first microprocessor may be a primary microprocessor. The one or more applications written in the first computer language may be one or more primary applications. The second microprocessor may be a safety microprocessor. The one or more applications written in the second computer language may be one or more safety applications.

The first computer language may be chosen from the group consisting of Ada, Basic, Cobol, C, C++, C#, Fortran, Visual Assembler, Visual Basic, Visual J++, Java, and Java Script. The second computer language may be chosen from the group consisting of Ada, Basic, Cobol, C, C++, C#, Fortran, Visual Assembler, Visual Basic, Visual J++, Java, and Java Script.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

Figure 1:
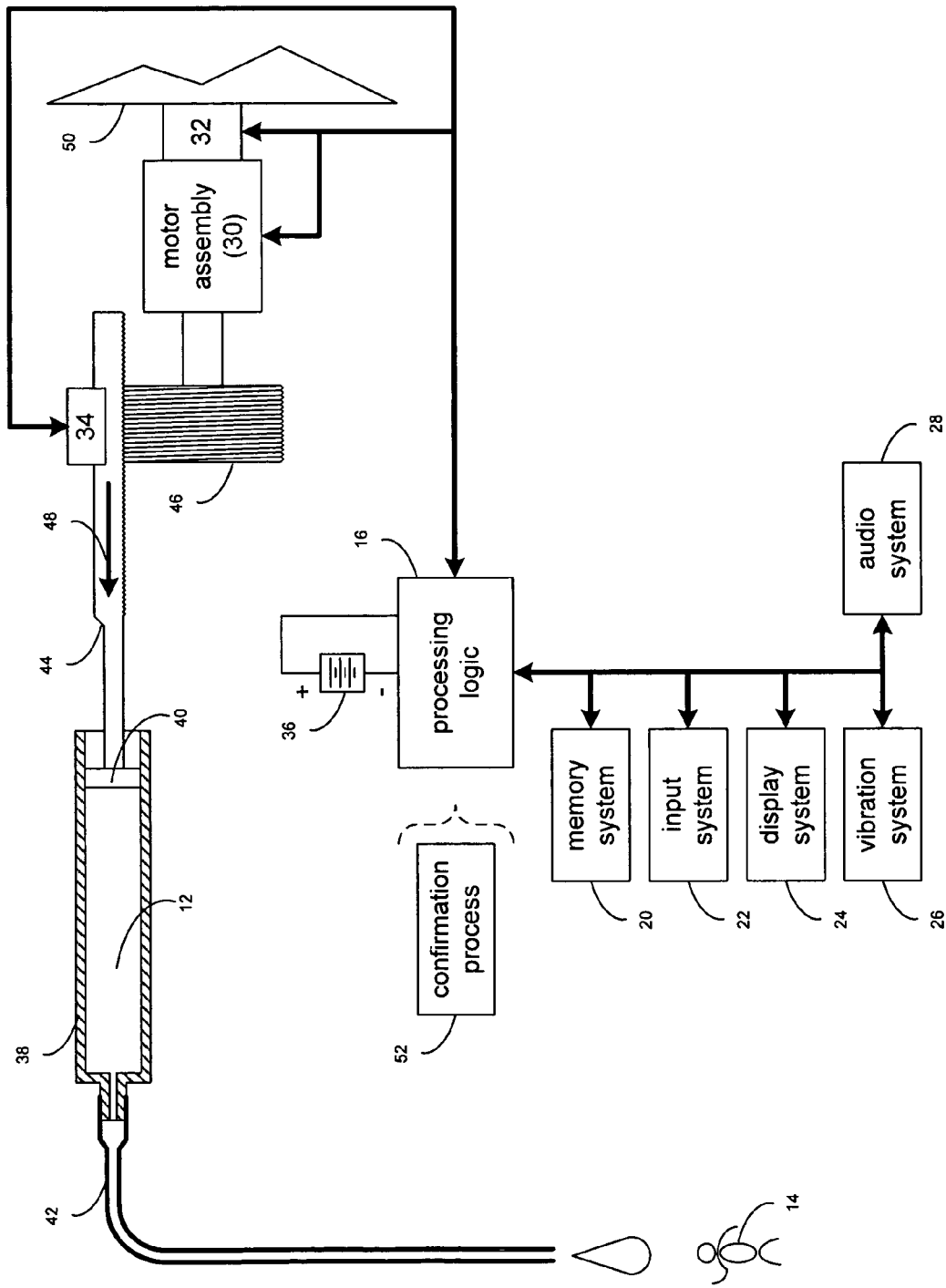
FIG. 1 is a diagrammatic view of an infusion pump assembly including processing logic that executes a confirmation process.

Referring to FIG. 1, there is shown in infusion pump assembly 10 that may be configured to deliver infusible fluid 12 to user 14. As discussed above, infusible fluid 12 may be delivered intravenously (i.e., into a vein), subcutaneously (i.e., into the skin), arterially (i.e., into an artery), and epidurally (i.e., into the epidural space). Examples of infusible fluid 12 may include but are not limited to insulin, nutrients, saline solution, antibiotics, analgesics, anesthetics, hormones, vasoactive drugs, and chelation drugs Infusion pump assembly 10 may include processing logic 16 that executes one or more processes that may be required for infusion pump assembly 10 to operate properly. Processing logic 16 may include one or more microprocessors (to be discussed below in greater detail), one or more input/output controllers (not shown), and cache memory devices (not shown). One or more data buses and/or memory buses may be used to interconnect processing logic 16 with one or more subsystems.

Examples of such subsystems may include but are not limited to memory system 20, input system 22, display system 24, vibration system 26, audio system 28, motor assembly 30, force sensor 32, and displacement detection device 34. Infusion pump assembly 10 may include primary power supply 36 (e.g. a first battery) for providing electrical power to at least a portion of processing logic 16 and one or more of the subsystems (e.g., memory system 20, input system 22, display system 24, vibration system 26, audio system 28, motor assembly 30, force sensor 32, and displacement detection device 34).

Infusion pump assembly 10 may include reservoir assembly 38 configured to contain infusible fluid 12. In some embodiments, the reservoir assembly 38 may be a reservoir assembly similar to that described in U.S. Patent Application Publication No. US-2004-0135078-A1, published Jul. 15, 2004, which is herein incorporated by reference in its entirety. In other embodiments, the reservoir assembly may be any assembly in which fluid may be acted upon such that at least a portion of the fluid may flow out of the reservoir assembly, for example, the reservoir assembly, in various embodiments, may include but is not limited to: a barrel with a plunger, a cassette or a container at least partially constructed of a flexible membrane.

Plunger assembly 40 may be configured to displace infusible fluid 12 from reservoir assembly 38 through cannula assembly 42 so that infusible fluid 12 may be delivered to user 14. In this particular embodiment, plunger assembly 40 is shown to be displaceable by partial nut assembly 44, which may engage lead screw assembly 46 that may be rotatable by motor assembly 30 in response to signals received from processing logic 16. In this particular embodiment, the combination of motor assembly 30, plunger assembly 40, partial nut assembly 44, and lead screw assembly 46 may form a pump assembly that effectuates the dispensing of infusible fluid 12 contained within reservoir assembly 38. An example of partial nut assembly 44 may include but is not limited to a nut assembly that is configured to wrap around lead screw assembly 46 by e.g., 30 degrees. In some embodiments, the pump assembly may be similar to one described in U.S. Pat. No. 7,306,578, issued Dec. 11, 2007, which is herein incorporated by reference in its entirety.

During operation of infusion pump assembly 10, infusible fluid 12 may be delivered to user 14 in accordance with e.g. a defined delivery schedule. For illustrative purposes only, assume that infusion pump assembly 10 is configured to provide 0.00025 mL of infusible fluid 12 to user 14 every three minutes. Accordingly, every three minutes, processing logic 16 may provide the power to motor assembly 30 to allow motor assembly 30 to rotate lead screw assembly 46 the appropriate amount so that partial nut assembly 44 (and therefore plunger assembly 40) may be displaced the appropriate amount in the direction of arrow 48 so that 0.00025 mL of infusible fluid 12 are provided to user 14 (via cannula 42). It should be understood that the volume of infusible fluid 12 that may be provided to user 14 may vary based upon, at least in part, the nature of the infusible fluid (e.g., the type of fluid, concentration, etc.), use parameters (e.g., treatment type, dosage, etc.), as well as various other factors that will be understood by one having skill in the art. As such, the foregoing illustrative example should not be construed as a limitation of the present disclosure.

Force sensor 32 may be configured to provide processing logic 16 with data concerning the force required to drive plunger assembly 40 into reservoir assembly 38. Force sensor 32 may include one or more strain gauges and/or pressure sensing gauges and may be positioned between motor assembly 30 and an immovable object (e.g. bracket assembly 50) included within infusion pump assembly 10.

In one embodiment, force sensor 32 includes four strain gauges (not shown), such that: two of the four strain gauges are configured to be compressed when driving plunger 40 into reservoir assembly 38; and two of the four strain gauges are configured to be stretched when driving plunger 40 into reservoir assembly 38. The four strain gauges (not shown) may be connected to a Wheatstone Bridge (not shown) that produces an analog force signal (not shown) that is a function of the pressure sensed by force sensor 32. The analog force signal (not shown) produced by force sensor 32 may be provided to an analog-to-digital converter (not shown) that may convert the analog force signal (not shown) into a digital force signal (not shown) that may be provided to processing logic 16. An amplifier assembly (not shown) may be positioned prior to the above-described analog-to-digital converter and may be configured to amplify the output of e.g., force sensor 32 to a level sufficient to be processed by the above-described analog-to-digital converter.

Motor assembly 30 may be configured as e.g., a brush-type DC electric motor. Further, motor assembly 30 may include a reduction gear assembly (not shown) that e.g. requires motor assembly 30 to rotate e.g., three-thousand revolutions for each revolution of lead screw assembly 46, thus increasing the torque and resolution of motor assembly 30 by a factor of three-thousand.

Figure 2:
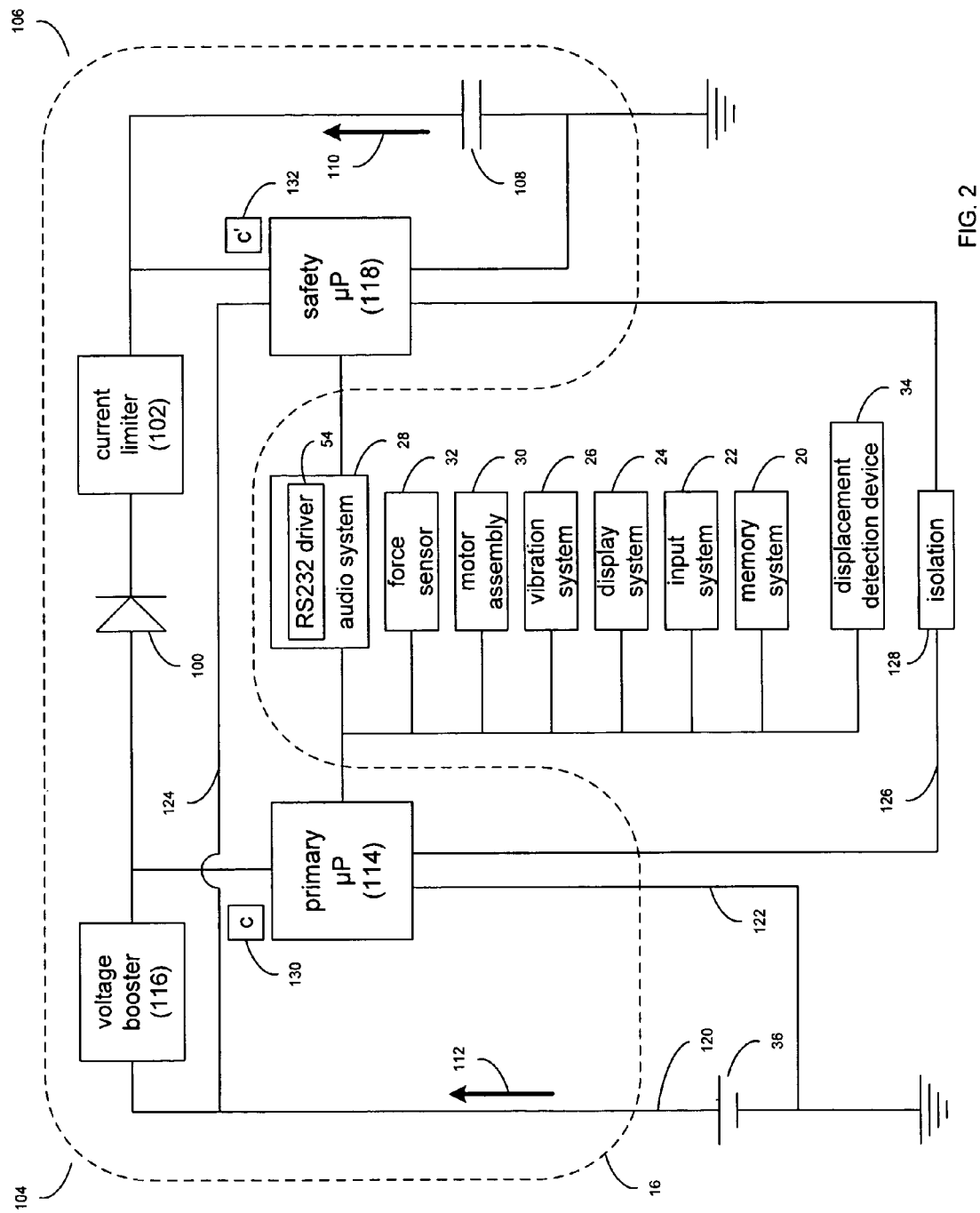
FIG. 2 is a more-detailed diagrammatic view of the processing logic of FIG. 1.

Referring also to FIG. 2, there is shown a more-detailed diagrammatic view of processing logic 16. Processing logic 16 may include one or more circuit partitioning components 100, 102 configured to divide processing logic 16 into primary processing logic 104 and backup processing logic 106. Examples of one or more circuit partitioning components 100, 102 may include but are not limited to diode assembly 100 and current limiting assembly 102.

Diode assembly 100 may be configured to allow primary power supply 36 to charge backup power supply 108 included within backup processing logic 106, while prohibiting backup power supply 108 from providing backup electrical energy 110 to primary processing logic 104 in the event that some form of failure prevents primary electrical energy 112 from providing primary processing logic 104. An example of backup power supply 108 may include but is not limited to a super capacitor assembly. An example of such a super capacitor assembly may include but is not limited to an electric double-layer capacitor manufactured by Elna Co. Ltd. of Yokohama, Japan.

Current limiting assembly 102 may be configured to limit the amount of primary electrical energy 112 available to charge backup power supply 108. Specifically, as primary power supply 36 may be configured to charge backup power supply 108, the amount of current available from primary power supply 36 may be limited to e.g., avoid depriving primary processing logic 104 of a requisite portion of primary electrical energy 112.

Primary processing logic 104 may include primary microprocessor 114 and voltage booster circuit 116. An example of primary microprocessor 114 may include but is not limited to a H8S/2000 manufactured by Renesas Technology America Inc. of San Jose, Calif. Voltage booster circuit 116 may be configured to increase the voltage potential of primary electrical energy 112 provided by primary power supply 36 to a level sufficient to power primary microprocessor 114. An example of voltage booster circuit 116 may include but is not limited to a LTC3421 manufactured by Linear Technology of Milpitas, Calif.

Current limiting assembly 102 may be configured to limit the amount of current available to charge backup power supply 108 during the power-up of primary microprocessor 114. Specifically and for illustrative purposes, current limiter assembly 102 may be controlled by primary microprocessor 114 and current limiting assembly 102 may be disabled (i.e., provide no charging current to backup power supply 108) until after primary microprocessor 114 is fully powered up. Upon primary microprocessor 114 being fully powered up, primary microprocessor 114 may now enable current limiting assembly 102, thus providing charging current to backup power supply 108. Alternatively and upon being initially energized, current limiting assembly 102 may be configured to prohibit the flow of charging current to backup power supply 108 for a time sufficient to allow for the powering up of primary microprocessor 114.

Backup processing logic 106 may include backup power supply 108 and safety microprocessor 118. An example of safety microprocessor 118 may include but is not limited to a MSP430 manufactured by Texas Instruments of Dallas, Tex.

Primary power supply 36 may be configured to provide primary electrical energy 112 to at least a portion of processing logic 16. Specifically and during normal operation of infusion pump assembly 10, primary power supply 36 may be configured to provide primary electrical energy 112 to all of processing logic 16 (including the various components of primary processing logic 104 and backup processing logic 106), as well as various subsystems included within infusion pump assembly 10.

Examples of such subsystems may include but are not limited to memory system 20, input system 22, display system 24, vibration system 26, audio system 28, motor assembly 30, force sensor 32, and displacement detection device 34.

Backup power supply 108 may be configured to provide backup electrical energy 110 to the at least a portion of processing logic 16 in the event that primary power supply 36 fails to provide primary electrical energy 112 to at least a portion of processing logic 16. Specifically, in the event that primary power supply 36 fails and, therefore, can no longer provide primary electrical energy 112 to processing logic 16, backup power supply 108 may be configured to provide backup electrical energy 110 to backup processing logic 106.

For illustrative purposes only, assume that infusion pump assembly 10 is operating normally and primary power supply 36 is providing primary electrical energy 112 to processing logic 16. As discussed above, voltage booster circuit 116 may increase the voltage potential of primary electrical energy 112 to a level sufficient to power primary microprocessor 114, wherein voltage booster circuit 116 and primary microprocessor 114 are both included within primary processing logic 104.

Further, diode assembly 100 may allow a portion of primary electrical energy 112 to enter backup processing logic 106, thus enabling the operation of safety microprocessor 118 and the charging of backup power supply 108. As discussed above an example of backup power supply 108 may include but is not limited to a super capacitor. As discussed above, current limiter assembly 102 may limit the quantity of current provided by primary power supply 36 to backup processing logic 106, thus preventing the diversion of too large a portion of primary electrical energy 112 from primary processing logic 104 to backup processing logic 106.

Accordingly, in addition to powering safety microprocessor 118, primary power supply 36 may charge backup power supply 108. In a preferred embodiment, backup power supply 108 is a 0.33 farad super capacitor.

Safety microprocessor 118 may monitor the status of primary power supply 36 by monitoring the voltage potential present at the input of voltage booster circuit 116. Alternatively, safety microprocessor 118 may monitor the status of primary power supply 36 by e.g. monitoring (via conductor 124) the voltage potential present at the output of voltage booster circuit 116. Alternatively, safety microprocessor 118 may monitor the status of primary power supply 36 by monitoring the voltage potential present at the input of voltage booster circuit 116. Further still, safety microprocessor 118 and primary microprocessor 114 may be electrically-coupled via e.g. conductor 126 and primary microprocessor 114 may be configured to continuously provide a "beacon" signal to safety microprocessor 118. Conductor 126 may include isolation circuit 128 (e.g., one or more diodes assemblies) to electrically isolate safety microprocessor 118 and primary microprocessor 114. Accordingly, provided safety microprocessor 118 continues to receive the "beacon" signal from primary microprocessor 114, primary microprocessor 114 is functioning and, therefore, being properly powered by primary power supply 36. In the event that safety microprocessor 118 fails to receive the "beacon" signal from primary microprocessor 114, an alarm sequence may be initiated.

Further still, safety microprocessor 118 may be configured to continuously provide a "beacon" signal to primary microprocessor 114. Accordingly, provided primary microprocessor 114 continues to receive the "beacon" signal from safety microprocessor 118, safety microprocessor 118 is functioning and, therefore, being properly powered by backup power supply 108. In the event that primary microprocessor 114 fails to receive the "beacon" signal from safety microprocessor 118, an alarm sequence may be initiated.

As used in this disclosure, a "beacon" signal may be considered an event that is performed by primary microprocessor 114 (and/or safety microprocessor 118) solely for the purpose of making the presence of primary microprocessor 114 (and/or safety microprocessor 118) known. Additionally/alternatively, the "beacon" signal may be considered an event that is performed by primary microprocessor 114 (and/or safety microprocessor 118) for the purpose of performing a task, wherein the execution of this event is monitored by safety microprocessor 118 (and/or primary microprocessor 114) to confirm the presence of primary microprocessor 114 (and/or safety microprocessor 118).

Assume for illustrative purposes that primary power supply 36 fails. For example, assume that primary power supply 36 physically fails (as opposed to simply becoming discharged). Examples of such a failure may include but are not limited to the failing of a cell (not shown) within primary power supply 36 and the failing of a conductor (e.g., one or more of conductors 120, 122) that electrically-couples primary power supply 36 to processing logic 16. Accordingly, in the event of such a failure, primary power supply 36 may no longer provide primary electrical energy 112 to processing logic 16.

However, when such a failure of primary power supply 36 occurs, the voltage potential present at the output of voltage booster circuit 116 and the voltage potential present at the input of voltage booster circuit 116 may be reduced to zero. Since safety microprocessor 118 may monitor (as discussed above) one or more of these voltage potentials, safety microprocessor 118 may be knowledgeable that primary power supply 36 has failed.

Further, when such a failure of primary power supply 36 occurs, primary microprocessor 114 will no longer be powered and, therefore, primary microprocessor 1141 will no longer produce the above-described "beacon" signals. Since safety microprocessor 118 monitors the above-described "beacon" signals, safety microprocessor 118 may be knowledgeable that primary power supply 36 has failed.

As discussed above, in the event of such a failure of primary power supply 36, as diode assembly 100 is reversed-biased, backup power supply 108 may not provide backup electrical energy 110 to primary processing logic 104. Accordingly, primary processing logic 104 will know longer function.

Upon sensing the failure of primary power supply 36, safety microprocessor 118 may initiate an alarm sequence that may result in audio system 28 being energized. Audio system 28 may be controllable by both safety microprocessor 118 and primary microprocessor 114. Alternatively, a separate audio system may be used for each of safety microprocessor 118 and primary microprocessor 114. An example of audio system 118 may include but is not limited to a Piezo electric diaphragm, an example of which may include but is not limited to a 7BB-15-6 manufactured by Murata of Kyoto, Japan.

Audio system 28 may further include an RS232 line driver circuit 54, such as a MAX3319/MAX3221 manufactured by Maxim Integrated Products of Sunnyvale, Calif. One or more of primary microprocessor 114 and safety microprocessor 118 may be configured to provide an alarm control signal (e.g., a square wave; not shown) to RS232 line driver circuit 52 to generate an alarm output signal (not shown) that may be provided to and may drive the above-described Piezo electric diaphragm.

The alarm sequence initiated by safety microprocessor 118 is intended to inform user 14 of the failure of primary power supply 36 so that user 14 may take the appropriate action (e.g. seeking an alterative means to have their therapy performed and/or having infusion pump assembly 10 repaired/replaced). Backup power supply 108 may be sized so that safety microprocessor 118 and audio system 28 may continue to function for up to fifteen minutes or more after the failure of primary power supply 36 (i.e., depending on design specifications).

The alarm sequence initiated by safety microprocessor 118 and/or primary microprocessor 114 may be an "escalating" alarm sequence in some embodiments. For example, at first a discrete "vibrating" alarm may be initiated (via vibration system 26). In the event that this "vibrating" alarm is not acknowledged within a defined period of time (e.g., one minute), a low volume audible alarm may be initiated. In the event that this low volume alarm is not acknowledged within a defined period of time (e.g., one minute), a medium volume audible alarm may be initiated. In the event that this medium volume alarm is not acknowledged within a defined period of time (e.g., one minute), a high volume audible alarm may be initiated. The escalating alarm sequence may provide a notification to user 14, in which the notification may be discrete or less disruptive at the onset. The initially discrete or less disruptive notification may be advantageous as user 14 may experience minimal disruption. However, in the event that user 14 does not acknowledge the alarm, the escalating nature of the alarm may provide for additional layers of safety to user 14. Additionally, in a case of audio system 28 error, or vibration system 26 error, the escalating alarm sequence, which may include both vibration and audio alarms, may insure that user 14 may be notified regardless of whether both systems 26, 28 are functioning.

Audio system 28, in some embodiments, may be configured to perform a self test upon power up. For example, upon infusion pump assembly 10 being initially powered up, audio system 28 may provide a "beep-type" signal to each sound generating device included within audio system 28. In the event that user 14 does not hear these "beep-type" signal(s), user 14 may take the appropriate action (e.g. seeking an alterative means to have their therapy performed and/or having infusion pump assembly 10 repaired/replaced). As discussed above, audio system 28 may be controllable by safety microprocessor 118 and/or primary micro-processor 114. Accordingly, when performing the above-described self test upon power up, safety microprocessor 118 and/or primary microprocessor 114 may control the above-described self test. This feature may provide for additional safety to user 14, as user 14 may be alerted to a system error earlier than may otherwise be the case. Thus, a method may be provided to notify the user early of system errors. Also, the system may otherwise not be aware of an error in audio system 28, thus, this feature provides for identification of a failure by user 14 that may otherwise go undetected.

During the failure of primary power supply 36, safety microprocessor 118 may continue to monitor the voltage potential present at the output of voltage booster circuit 116 and/or the voltage potential present at the input of voltage booster circuit 116. Additionally, safety microprocessor 118 may continue to monitor for the presence of the above-described "beacon" signals. Accordingly, in the event that the failure of primary power supply 36 was a temporary event (e.g. primary power supply 36 is an out-of-date battery and is being replaced with a new battery), safety microprocessor 118 may be knowledgeable when primary power supply 36 is once again functioning properly.

Upon primary power supply 36 once again functioning properly, diode assembly 100 and current limiting assembly 102 may allow a portion of primary electrical energy 112 produced by primary power supply 36 to recharge backup power supply 108.

Additionally, safety microprocessor 118 and primary microprocessor 114 may each maintain a real-time clock, so that the various doses of infusible fluid may be dispensed at the appropriate time of day. As primary microprocessor 114 was not functioning during the failure of primary power supply 36, the real-time clock maintained within primary microprocessor 114 may no longer be accurate. Accordingly, the real-time clock maintained within safety microprocessor 118 may be used to reset the real-time clock maintained within primary microprocessor 114.

In order to further enhance the reliability and safety of infusion pump assembly 10, primary microprocessor 114 and safety microprocessor 118 may each execute applications written in different programming languages. For example, primary microprocessor 114 may be configured to execute one or more primary applications written in a first computer language, while safety microprocessor 118 may be configured to execute one or more safety applications written in a second computer language.

Examples of the first computer language in which the primary applications are written may include but are not limited to Ada, Basic, Cobol, C, C++, C#, Fortran, Visual Assembler, Visual Basic, Visual J++, Java, and Java Script languages. In a preferred embodiment, the first computer language in which the primary applications (executed on primary microprocessor 114) are written is the C++ computer language.

Examples of the second computer language in which the safety applications are written may include but are not limited to Ada, Basic, Cobol, C, C++, C#, Fortran, Visual Assembler, Visual Basic, Visual J++, Java, and Java Script languages. In a preferred embodiment, the second computer language in which the safety applications (executed on safety microprocessor 118) are written is the C computer language.

Further, assuming that primary microprocessor 114 and safety microprocessor 118 are different types of microprocessors and, therefore, use different compilers; the compiled code associated with the primary applications executed by primary microprocessor 114 and the safety applications executed on safety microprocessor 118 may be different (regardless of the whether the primary applications and the safety applications were written in the same computer language.

Examples of the one or more primary applications written in the first computer language and executable on primary microprocessor 114 may include but are not limited to an operating system (e.g., Linux™, Unix™, Windows CE™), an executive loop and various software applications. Further, examples of the one or more safety applications written in the second computer language and executable on safety microprocessor 118 may include but are not limited to an operating system (e.g., Linux™, Unix™, Windows CE™), an executive loop and various software applications.

Accordingly, primary processing logic 104 and backup processing logic 106 may each be configured as a separate stand-alone autonomous computing device. Therefore, primary microprocessor 114 included within primary processing logic 104 may execute a first operating system (e.g. Linux™) and safety microprocessor 118 included within backup processing logic 106 may execute an executive loop.

Additionally, primary microprocessor 114 included within primary processing logic 104 may execute one or more software applications (e.g. graphical user interface applications, scheduling applications, control applications, telemetry applications) executable within (in this example) a Linux™ operating system. Further, safety microprocessor 118 included within backup processing logic 106 may execute one or more software applications (e.g. graphical user interface applications, scheduling applications, control applications, telemetry applications) executable within (in this example) the executive loop.

By utilizing diverse computer languages and/or diverse operating systems, infusion pump assembly may be less susceptible to e.g. computer-language bugs, operating-system bugs, and/or computer viruses.

One or more of primary microprocessor 114 (included within primary processing logic 104 of processing logic 16) and safety microprocessor 118 (included within backup processing logic 106 of processing logic 16) may execute confirmation process 52 (FIG. 1). As will be discussed below in greater detail, confirmation process 52 may be configured to process a command received on a first microprocessor (e.g., primary microprocessor 114) so that the command may be confirmed by a second microprocessor (e.g., safety microprocessor 118).

The instruction sets and subroutines of confirmation process 52, which may be stored on a storage device (e.g., memory system 20) accessible by processing logic 16, may be executed by one or more processors (e.g., primary microprocessor 114 and/or safety microprocessor 118) and one or more memory architectures (e.g., memory system 20) included within infusion pump assembly 10. Examples of memory system 20 may include but are not limited to: a random access memory; a read-only memory; and a flash memory.

Figure 3:
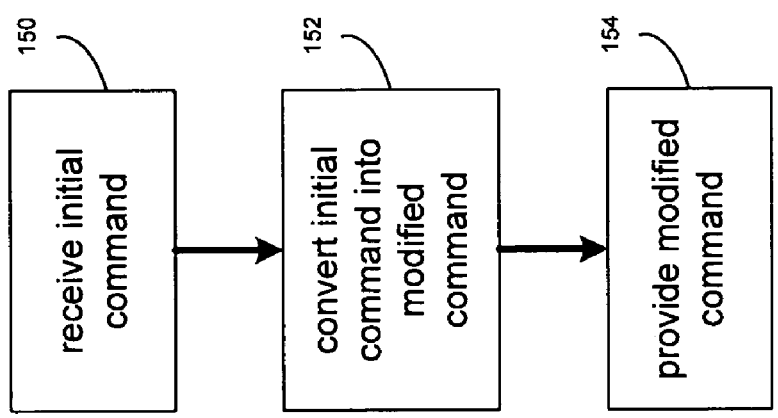
FIG. 3 is a flowchart of the confirmation process of FIG. 1.

Referring also to FIG. 3, confirmation process 52 may receive 150, on a first microprocessor executing one or more applications written in a first computer language, an initial command processable by the one or more applications written in the first computer language. For example and as discussed above, primary microprocessor 114 (included within primary processing logic 104) may be executing the Linux™ operating system. Assuming that user 14 wishes to have a 0.50 mL dose of infusible fluid 12 dispensed by infusion pump assembly 12, user 14 may select (via input system 22 and display system 24) the appropriate commands to have the 0.50 mL dose dispensed. Accordingly, primary microprocessor 114 may receive 150 a corresponding command (e.g., command 130) to dispense 0.50 mL of infusible fluid 12.

As discussed above, safety microprocessor 118 (included within backup processing logic 106) may be executing the executive loop. Accordingly, command 130 may not be provided to safety microprocessor 118 in its native form, as safety microprocessor 118 may not be capable of processing command 130, due to safety microprocessor 118 executing the executive loop and primary microprocessor 114 executing the Linux™ operating system.

Accordingly, confirmation process 52 may convert 152 initial command 130 into a modified command (e.g., command 132) that may be processable by e.g., safety microprocessor 118 (included within backup processing logic 106) that may be executing the executive loop. For example, confirmation process 52 may convert 152 initial command 130 into modified command 132 that is transmittable via a communication protocol (not shown) that effectuates the communication of primary microprocessor 114 and safety microprocessor 118. Once command 130 is converted 152 into modified command 132, modified command 132 may be provided 154 to e.g., safety microprocessor 118 (included within backup processing logic 106) that may be executing e.g., the executive loop.

Once received by e.g., safety microprocessor 118 (included within backup processing logic 106), safety microprocessor 118 may process modified command 132 and provide (via e.g., display system 24) a visual confirmation to user 14. Prior to processing modified command 132, confirmation process 52 may convert modified command 132 into a native command (not shown) processable by safety microprocessor 118. For example, upon receiving modified command 132, safety microprocessor 118 may process received modified command 132 to render (on display system 24) a visual confirmation.

Upon processing modified command 132, confirmation process 52 may render on display system 24 a message that states "Dispense 0.50 U Dose?". Upon reading this message, user 14 may either authorize the dispensing of the 0.50 mL dose or cancel the dispensing of the 0.50 mL dose. Accordingly, if user 14 authorizes the dispensing of the 0.50 mL dose of infusible fluid 12, the accuracy of command 130 and command 132 are both confirmed. However, in the event that e.g., the message rendered by confirmation process 52 is incorrect (e.g., "Dispense 1.50 U Dose?"), the conversion 152 of command 130 to command 132 has failed. Accordingly, primary microprocessor 114 (and/or the applications being executed on primary microprocessor 114) and/or safety microprocessor 118 (and/or the applications being executed on safety microprocessor 118) may be malfunctioning. Accordingly, user 14 may need to seek an alterative means to having their therapy performed and/or have infusion pump assembly 10 serviced. Accordingly, the operational safety and reliability of infusion pump assembly 10 may be enhanced as any command received is confirmed as being correct by both primary microprocessor 114, safety microprocessor 118, and user 14.

A number of implementations have been described. Nevertheless, it will be understood that various modifications may be made. Accordingly, other implementations are within the scope of the following claims.

What is claimed is:

1. An infusion pump assembly comprising:
    a reservoir assembly configured to contain an infusible fluid;
    a motor assembly configured to act upon the reservoir assembly and dispense at least a portion of the infusible fluid contained within the reservoir assembly;
    processing logic configured to control the motor assembly;
    wherein the processing logic includes:
        a primary microprocessor configured to execute one or more primary applications written in a first computer language; and
        a safety microprocessor configured to execute one or more safety applications written in a second computer language that is different than the first computer language.

2. The infusion pump assembly of claim 1 further comprising:
    a primary power supply configured to provide primary electrical energy to at least a portion of the processing logic; and
    a backup power supply configured to provide backup electrical energy to the at least a portion of the processing logic in the event that the primary power supply fails to provide the primary electrical energy to the at least a portion of the processing logic.

3. The infusion pump assembly of claim 1 wherein:
    the primary power supply is a first battery; and
    the backup power supply is a super capacitor assembly.

4. The infusion pump assembly of claim 1 wherein the processing logic includes one or more circuit partitioning components configured to divide the processing logic into primary processing logic and backup processing logic.

5. The infusion pump assembly of claim 4 wherein the primary processing logic includes the primary microprocessor.

6. The infusion pump assembly of claim 4 wherein the backup processing logic includes the safety microprocessor.

7. The infusion pump assembly of claim 4 wherein the one or more circuit partitioning components includes one or more of a diode assembly and a current limiting assembly.

8. The infusion pump assembly of claim 7 wherein the diode assembly is configured to allow the primary power supply to charge the backup power supply while prohibiting the backup power supply from providing backup electrical energy to the primary processing logic in the event that the primary power supply fails to provide the primary electrical energy to the primary processing logic.

9. The infusion pump assembly of claim 1 wherein the one or more primary applications written in the first computer language are chosen from the group consisting of an operating system, an executive loop and a software application.

10. The infusion pump assembly of claim 1 wherein the one or more safety applications written in the second computer language are chosen from the group consisting of an operating system, an executive loop and a software application.

11. The infusion pump assembly of claim 1 wherein the primary power supply is configured to provide electrical energy to one or more subsystems included within the infusion pump assembly.

12. The infusion pump assembly of claim 1 wherein the primary power supply and the backup power supply are configured to provide electrical energy to an audio system included within the infusion pump assembly.

13. The infusion pump assembly of claim 1 wherein the audio system is configured to provide an escalating alarm sequence in the event of a loss of a beacon signal, wherein the escalating alarm sequence includes at least a low-intensity alarm and a high-intensity alarm.

14. The infusion pump assembly of claim 1 wherein the first computer language is chosen from the group consisting of Ada, Basic, Cobol, C, C++, C#, Fortran, Visual Assembler, Visual Basic, Visual J++, Java, and Java Script.

15. The infusion pump assembly of claim 1 wherein the second computer language is chosen from the group consisting of Ada, Basic, Cobol, C, C++, C#, Fortran, Visual Assembler, Visual Basic, Visual J++, Java, and Java Script.

16. An infusion pump assembly comprising:
   a reservoir assembly configured to contain an infusible fluid;
   a motor assembly configured to act upon the reservoir assembly and dispense at least a portion of the infusible fluid contained within the reservoir assembly;
   processing logic configured to control the motor assembly; wherein the processing logic includes:
      one or more circuit partitioning components configured to divide the processing logic into primary processing logic and backup processing logic;
      a primary microprocessor included within the primary processing logic and configured to execute one or more primary applications written in a first computer language; and
      a safety microprocessor included within the backup processing logic and configured to execute one or more safety applications written in a second computer language that is different than the first computer language.

17. The infusion pump assembly of claim 16 wherein the one or more primary applications written in the first computer language are chosen from the group consisting of an operating system, an executive loop and a software application.

18. The infusion pump assembly of claim 16 wherein the one or more safety applications written in the second computer language are chosen from the group consisting of an operating system, an executive loop and a software application.

19. The infusion pump assembly of claim 16 further comprising:
   a primary power supply configured to provide primary electrical energy to at least a portion of the processing logic; and
   a backup power supply configured to provide backup electrical energy to the at least a portion of the processing logic in the event that the primary power supply fails to provide the primary electrical energy to the at least a portion of the processing logic.

20. The infusion pump assembly of claim 16 wherein the first computer language is chosen from the group consisting of Ada, Basic, Cobol, C, C++, C#, Fortran, Visual Assembler, Visual Basic, Visual J++, Java, and Java Script.

21. The infusion pump assembly of claim 16 wherein the second computer language is chosen from the group consisting of Ada, Basic, Cobol, C, C++, C#, Fortran, Visual Assembler, Visual Basic, Visual J++, Java, and Java Script.

\* \* \* \* \*